United States Patent

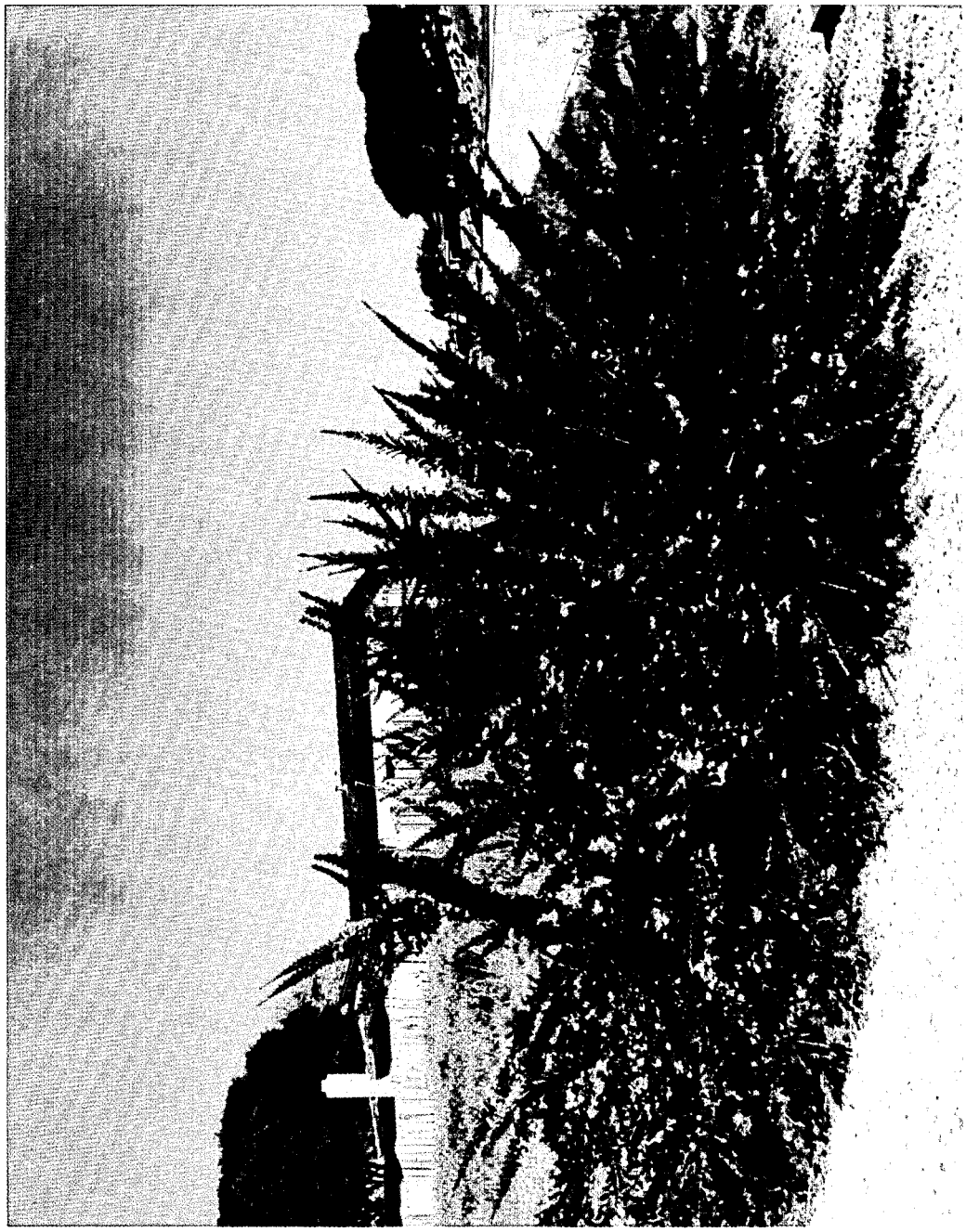

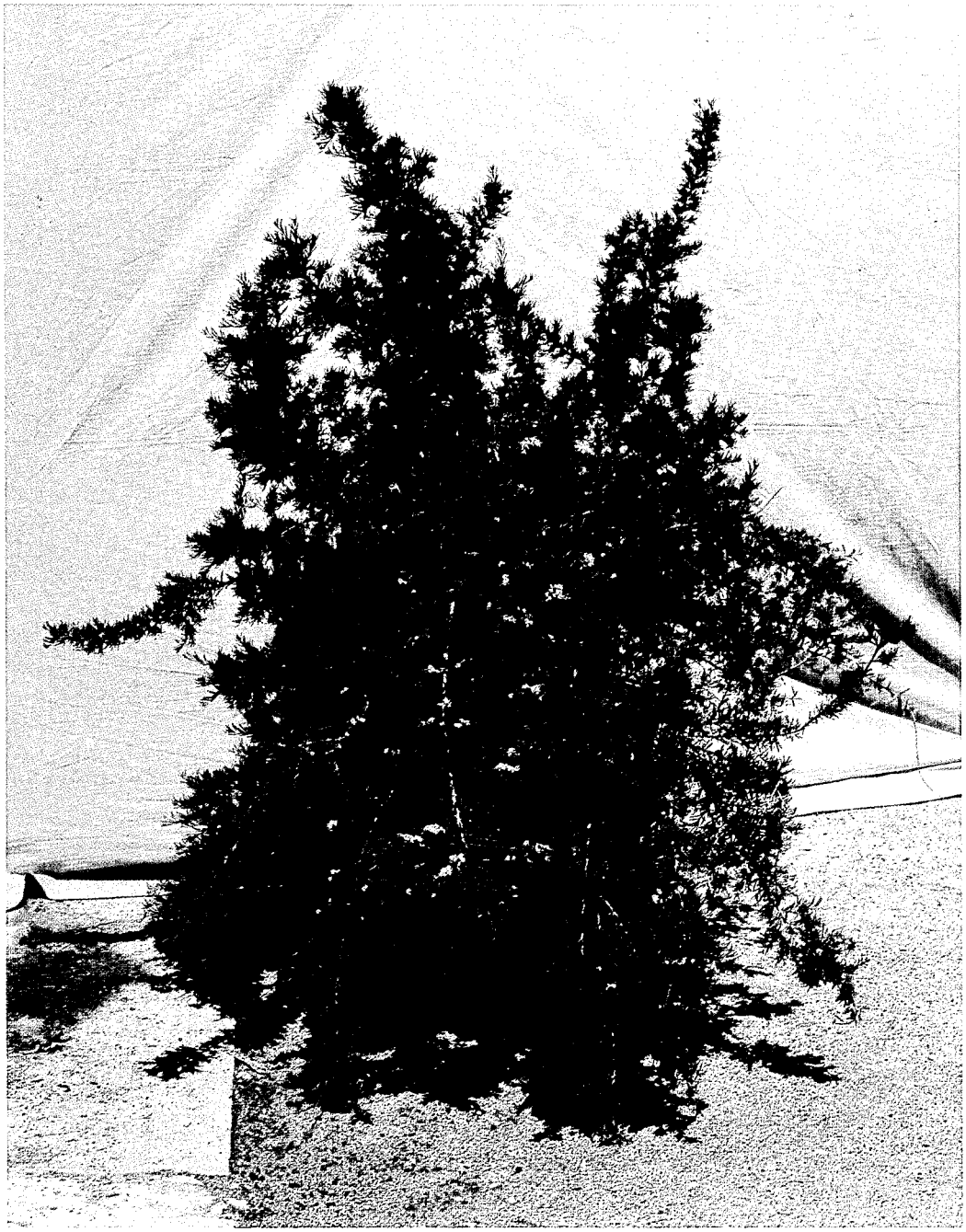

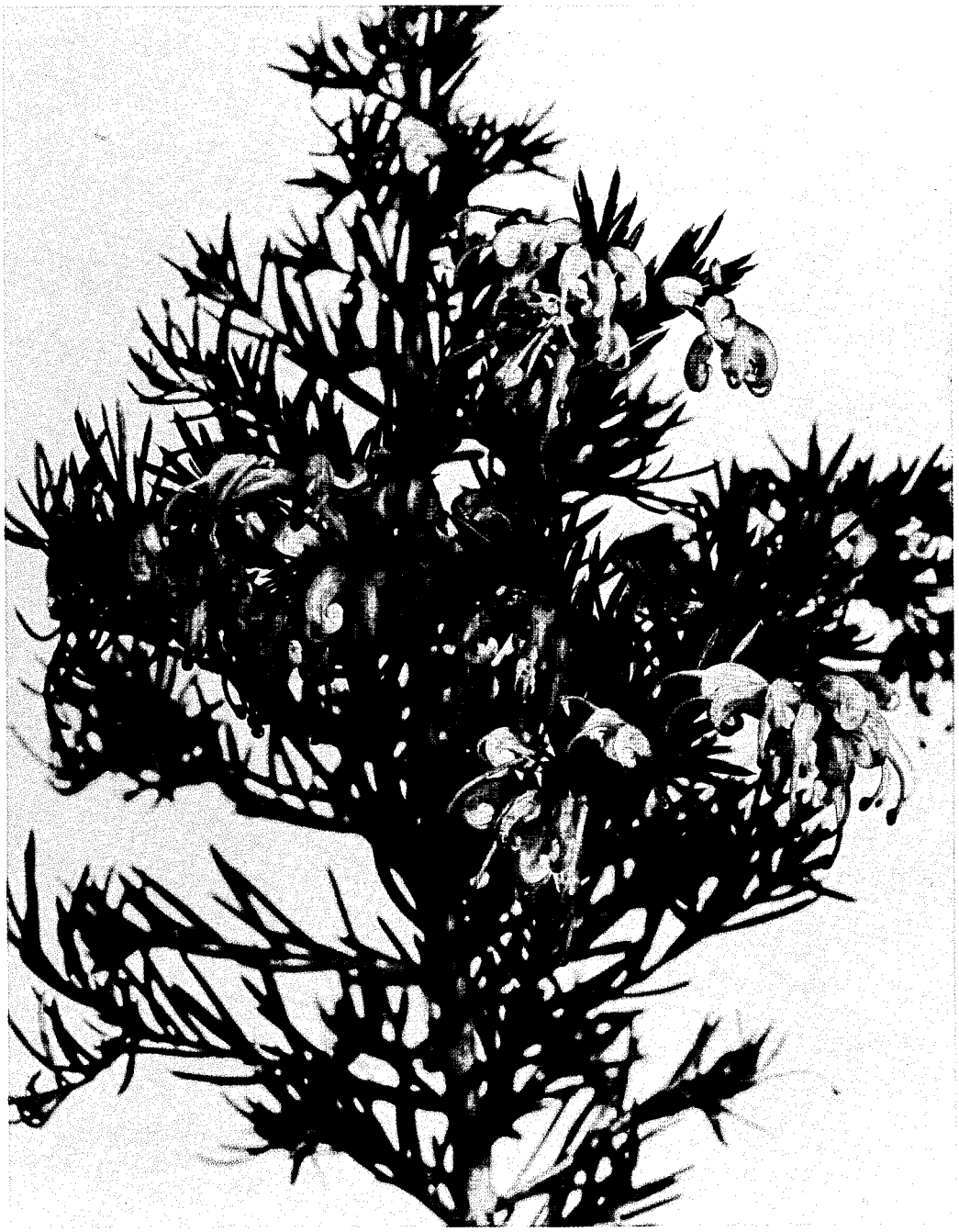

Plant Pat. 3,953

Patented Oct. 12, 1976

3,953

GREVILLEA PLANT AROMAS

Joseph Solomone, P.O. Box 1307, Watsonville, Calif. 95076

Filed Feb. 28, 1975, Ser. No. 554,234

Int. Cl.[2] A01H *5/02*

U.S. Cl. Plt.—54 1 Claim

The present invention relates to a new and distinct variety of Grevillea plant, which I first encountered as a seedling of an unnamed and unpatented variety of Grevillea "Noelli."

The drawings show a clump, a close-up of the inflorescence and a single plant of the instant variety.

At the time of my discovery, I was growing in my nursery in Watsonville, Calif., a block of Grevillea "Noelli" seedlings. As these seedlings matured and bloomed for the first time, one in particular attracted my attention. This plant differed from all the others in respect to the color and profuseness of its flowers, the size and stature of the plant, and other factors.

As soon as this distinctive seedling had attained a reasonable size, I took cuttings from it and succeeded in cloning a group of healthy progeny, which were identical in all aspects to their unique parent.

I then kept these new cultivars and the parent under observation, to be sure that their distinctive characteristics would remain stable. I also made observations regarding their hardiness: resistance to cold, drought, insects and disease.

These observations fully confirmed the unique characteristics of the new cultivar, as evidenced by the following combination of unique and outstanding features and which distinguish the new seedling from its parent, as well as from all other Grevillea varieties of which I am aware:

(1) The overall stature of the plant is larger and fuller (a true medium-sized shrub) than the parent Grevillea "Noelli";

(2) The plant has branches straight and rigidly erect, spreading, and the lower branches horizontal;

(3) The foliage is denser and more bristly, with the leaves stiffer than those of the parent plant;

(4) The inflorescences are much fuller, with profuse blooming over a longer period of time in comparison to the parent plant;

(5) The blossoms of the plant are a more intense and deeper red color than the parent plant, with a lesser amount of white appearing on the floral envelope.

The following is a detailed description of my new Grevillea plant:

Locality where grown and observed: Watsonville, Calif.

Propagations: Holds its distinguishing characteristics through succeeding progations by cuttings.

Plant:

*Form.*—Woody, medium-sized shrub.

*Habit.*—Shrub with stiff but stringy, erect or spreading branches, the lower one horizontal.

*Growth.*—Attains a height of about 2 m. at maturity, and spreads across up to 2.75 m.

*Foliage.*—Type: Needle-shaped, slightly revolute, apex spinescent, about 4 cm. long by .4 cm wide.

Phyllotaxy: Leaves alternate and spirally attached to a round stem. Color: Dorsal surface dark green; ventral surface light green; apex of leaves and entire stem dark red. Texture: Leaves glabrous and leathery; the stem pubescent. Aspect: Branches bristly, with stiff leaves, like a conifer.

*Flowers.*—Inflorescence type: a cluster (panicle) of short, condensed racemes. Color: The color range from carmen (21) to turkey red (721) from the Royal Horticultural Color Chart. Flowering period: Profuse blooms starting in December, lasting until August along the central California coastal region. Aspect: Plant blooms most profusely, giving an overall reddish appearance.

*Hardiness.*—Good, drought tolerant, enjoys direct sunlight, but cannot withstand prolonged periods of frost below −6° C.

*Pest and disease resistance.*—Excellent, by virtue of the fact that during several years of being in and around aphids, red mites, and so forth, this plant hasn't once contracted a disease or had any heavy infestation of insects. There has been no need to spray beyond the normal nursery schedule for pests.

*General observations.*—This new cultivar is useful for bank and erosion control, hedging, or as an accent plant in the garden. It grows well in containers or in the ground. It needs very little maintenance to keep it healthy and attractive.

The Grevillea Aromas can be differentiated from the *Grevillea banksi forsteri* and *Grevillea rosmarinifolia* as follows. *Grevillea banksi forsteri* has large compound (divided) leaves. In contrast, the plant of the present invention, Grevillea Aromas, has a simple leaf. Although there are other differences, this single difference clearly differentiates the two species.

*Grevillea rosmarinifolia* has leaves linear to 1½" long, margins revolute, densely silky, pubescent beneath, flowers in short dense racemes with peduncle ¼" to ⅜" long, ¼" long perianth. The racemes contain 7–12 flowers with most in the range of 8–10.

Grevilla Aromas, in contrast, has leaves linear to 1½" long, margins revolute, lightly silky, pubescent beneath, flowers in dense racemes with peduncle ¾" long, perianth ⅜" long, flowers in racemes 8–19 in number, mostly 10–15.

I claim:

1. A new and distinct variety of Grevillea as herein shown and described, characterized particularly as to novelty by the unique combination of a large and full stature, long slightly arched branches forming oblique angles with the ground, dense and bristly foliage with the leaves stiffer than usually encountered, the inflorescences very full, with profuse blooming over a long period of time, and the blossoms a very distinctive and deep red color, with a lesser amount of white appearing on the calyx of the flower.

No references cited.

ROBERT E. BAGWILL, Primary Examiner

JAMES R. FEYRER, Assistant Examiner